(12) United States Patent
Bode et al.

(10) Patent No.: US 7,712,376 B2
(45) Date of Patent: May 11, 2010

(54) METHOD FOR DETERMINING A PARAMETER CHARACTERISTIC OF THE FATIGUE STATE OF A PART

(75) Inventors: Andreas Bode, Höchstadt A. D. Aisch (DE); Edwin Gobrecht, Ratingen (DE)

(73) Assignee: Siemens Aktiengesellschaft-Muenchen (DE)

( * ) Notice: Subject to any disclaimer, the term of this patent is extended or adjusted under 35 U.S.C. 154(b) by 336 days.

(21) Appl. No.: 11/666,384

(22) PCT Filed: Oct. 26, 2005

(86) PCT No.: PCT/EP2005/055557

§ 371 (c)(1),
(2), (4) Date: Apr. 26, 2007

(87) PCT Pub. No.: WO2006/045811

PCT Pub. Date: May 4, 2006

(65) Prior Publication Data

US 2008/0107518 A1    May 8, 2008

(30) Foreign Application Priority Data

Oct. 29, 2004    (EP)    .................................. 04025821

(51) Int. Cl.
*G01M 15/14* (2006.01)
(52) U.S. Cl. ....................................................... 73/808
(58) Field of Classification Search ........................ None
See application file for complete search history.

(56) References Cited

U.S. PATENT DOCUMENTS

| | | | | |
|---|---|---|---|---|
| 3,588,265 A | | 6/1971 | Berry | |
| 4,764,882 A | * | 8/1988 | Braschel et al. | ................ 702/42 |
| 5,140,528 A | * | 8/1992 | Swaminathan et al. | ........ 702/34 |
| 5,517,424 A | * | 5/1996 | Marcelle et al. | ............. 700/287 |
| 5,748,500 A | * | 5/1998 | Quentin et al. | ............... 702/182 |
| 6,239,504 B1 | * | 5/2001 | Gobrecht et al. | .............. 290/52 |
| 6,512,982 B2 | * | 1/2003 | Yang et al. | ..................... 702/34 |
| 6,853,945 B2 | * | 2/2005 | Namburi | ...................... 702/130 |
| 6,915,635 B2 | * | 7/2005 | Wolf | ............................. 60/646 |
| 7,050,943 B2 | * | 5/2006 | Kauffman et al. | ............ 702/188 |
| 7,065,471 B2 | * | 6/2006 | Gotoh et al. | ................. 702/183 |
| 7,143,007 B2 | * | 11/2006 | Long et al. | ................... 702/184 |

(Continued)

FOREIGN PATENT DOCUMENTS

DE    30 38 552 A1    5/1982

(Continued)

*Primary Examiner*—Lisa M Caputo
*Assistant Examiner*—Freddie Kirkland, III

(57) ABSTRACT

A method for determining an approximate value for a parameter characteristic of the fatigue state of a component as a result of a time-varying stress to which it is subjected by means of a number of load cycles should, itself, during comparatively lengthy stress cycles, enable a prognosis concerning the current fatigue state of the component, this prognosis being, in particular, adapted to the needs and suited for the real-time determination of maintenance intervals. To this end, in addition to optionally already fully completed load cycles, a first partially completed load cycle is also taken into consideration during the determination of the parameter, whereby temporary stress values for phases that have not yet been run through of the partially completed load cycle are, together with a predetermined fixed value, taken into consideration.

8 Claims, 1 Drawing Sheet

U.S. PATENT DOCUMENTS

| | | | |
|---|---|---|---|
| 7,171,314 B2 * | 1/2007 | Meyer et al. | 702/42 |
| 7,467,070 B2 * | 12/2008 | Meyer et al. | 703/1 |
| 7,523,651 B2 * | 4/2009 | Bode | 73/112.01 |
| 2004/0148129 A1 | 7/2004 | Gotoh et al. | |

FOREIGN PATENT DOCUMENTS

| | | |
|---|---|---|
| DE | 40 06 948 A1 | 9/1991 |
| EP | 0 110 865 A2 | 6/1984 |
| EP | 0 937 194 B1 | 8/1999 |
| JP | 02038839 A1 | 2/1990 |
| JP | 2826598 B2 | 2/1990 |
| JP | 06257412 A | 9/1994 |

* cited by examiner

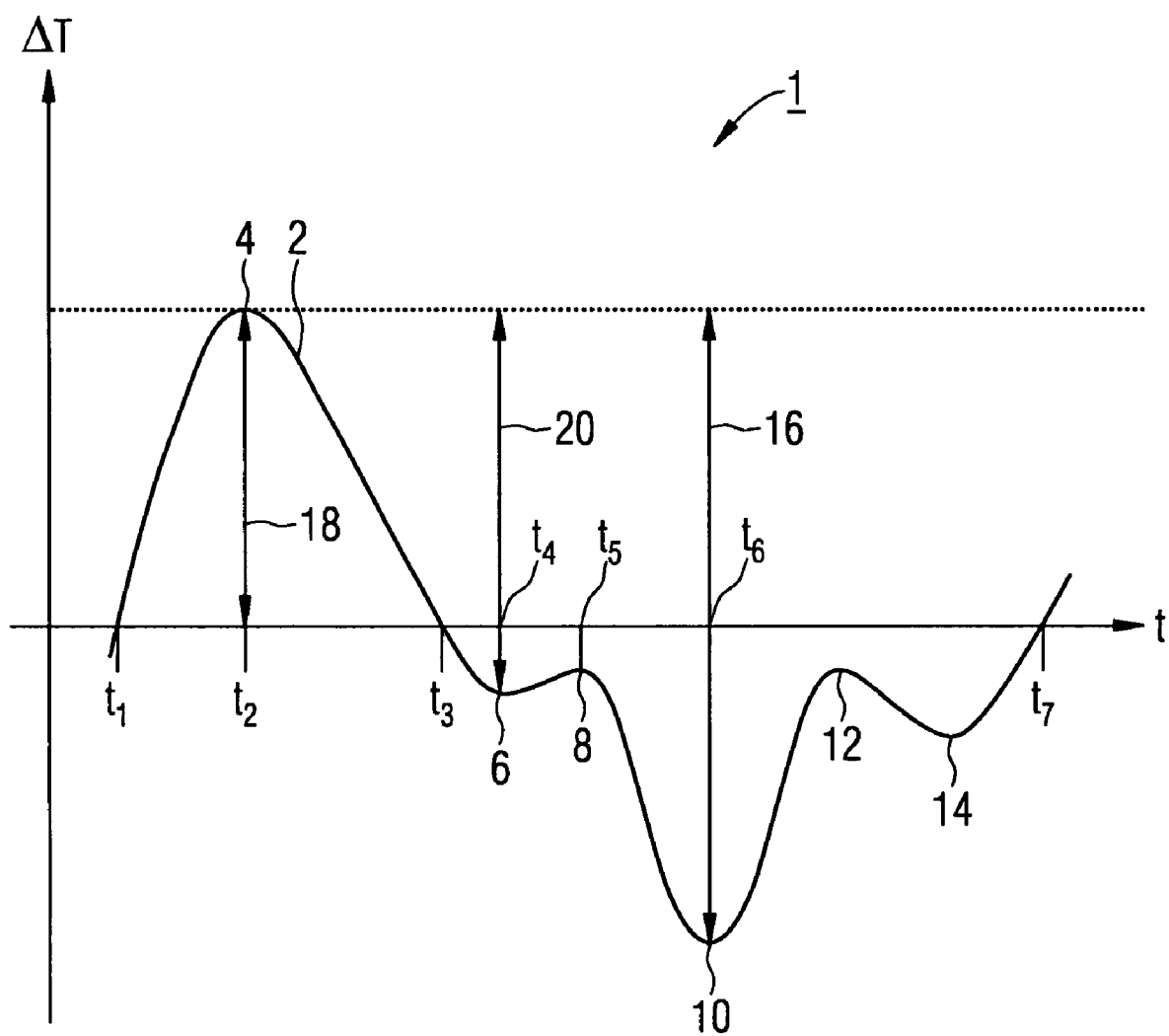

METHOD FOR DETERMINING A PARAMETER CHARACTERISTIC OF THE FATIGUE STATE OF A PART

CROSS REFERENCE TO RELATED APPLICATIONS

This application is the US National Stage of International Application No. PCT/EP2005/055557, filed Oct. 26, 2005 and claims the benefit thereof. The International Application claims the benefits of European application No. 04025821.2 EP filed Oct. 29, 2004, both of the applications are incorporated by reference herein in their entirety.

FIELD OF INVENTION

The invention relates to a method for determining an approximate value for a parameter characteristic of the fatigue state of a part. The fatigue state of the part is based upon time-varying stress by means of a number of load cycles.

BACKGROUND OF INVENTION

In a plurality of applications in technical systems parts or components can be subjected to stresses which alternate or vary over time, of a mechanical or thermal nature for example. In such cases individual parts can for example be subjected to direct mechanical stresses through the occurrence of compression or tensile forces. A time-varying thermal stress of this type arises on the other hand for example for the parts or components in a turbine system, especially in a steam turbine, when the steam turbine is started up or shut down.

This means that when the steam turbine is started up the turbine parts are increasingly heated up from a cold initial state until a comparatively high temperature level has been set during operation in accordance with design specifications. When the steam turbine is shut down on the other hand the parts start off in a comparatively hot initial state and are cooled down ever further until all components have reached the temperature of their surroundings. During this warming-up and cooling-down phase a temperature difference arises in a few parts between the surface directly exposed to the heating or cooling medium and the interior of the part concerned. These types of temperature difference can lead to thermal stresses in the part and thus to a direct load on the part.

The occurrence of mechanical or thermal loads of the type stated in the parts can lead at a microscopic level to rearrangement processes in the crystal structure of the parts or such like. The result of these types of time-varying loads is thus what is usually known as material fatigue or exhaustion of the part concerned, which is accompanied by a successive deterioration or detrimental effect on the material properties such as hardness or load capacity for example. As the fatigue state of the part or the associated detrimental effect on its material properties increase, the part concerned may possibly no longer meet the specific design criteria such as load capacity or similar for example, so that as a result of the ongoing fatigue of the component concerned with time-varying loading, its lifetime or future usability are restricted. For the parts subjected to an alternating or time-variant stress there is thus usually provision, taking into account the fatigue or material exhaustion occurring, for replacement of the component concerned in good time or also for other suitable maintenance within a predetermined maintenance interval.

To avoid unnecessary shutdowns of the relevant technical systems and the associated high maintenance costs and such like, or to keep said costs especially low, planning of maintenance intervals and such like adapted to the fatigue or exhaustion state of the part under particular load is usually provided. In order to achieve this in a particularly targeted fashion, provision is made for determining an approximate value of a parameter characteristic of the fatigue state of the part concerned. To determine a characteristic parameter of this type, the stress cycles of the part, also referred to as the load cycles, are evaluated. To do this the progress over time of the stress of the part concerned is monitored by continuously recording a measured value characteristic for it.

The disadvantage of the concept described is however that the measured values included for the determination of the characteristic parameter for the exhaustion state, particularly with stress cycles, which, depending on the use of the relevant part, can only be computed over s significant period of for example months or even years, can only be made available in a timely manner under some conditions.

SUMMARY OF INVENTION

An underlying object of the invention is thus to specify a method for determining a parameter for characterizing the fatigue state of a part as a result of time-varying stress on the basis of a number of load cycles, with which, even with comparatively extended load cycles over time, an especially appropriate and suitable prediction for timely definition of maintenance intervals relating to the current fatigue state of the part is made possible.

For example the progress over time of a mechanical tension affecting the part, or in the case of a steam turbine for example, the progress over time of a temperature difference arising in the part between the surface of the part and its interior, from which a thermal stress results, can be monitored. In this case a complete stress cycle of the part is referred to as the load cycle, in which, starting from an initial state, the curve passes through a maximum in the stress, occurring for example through a maximum mechanical tension, and subsequently, after a zero crossing, a minimum in the stress, occurring for example through a maximum mechanical compression force. The end point of this stress cycle referred to as the load cycle is reached when the part, after alternately undergoing tension and compression, has again reached its original state.

The overall load cycle occurring in such a stress cycle is in this case usually the overall range of variation of the stress passed through, i.e. the difference between the stress values when minimum compression force and maximum tension force are present. Based on empirical values, which are usually available on the one hand for specific materials and on the other for specific parts and can for example be stored in suitable material tables or such like, a characteristic parameter which specifies the associated material fatigue is determined from this type of load cycle after completion of the relevant stress cycle. The overall fatigue or exhaustion which occurs during the use of a part is calculated in this case by the accumulation of the individual characteristic fatigue parameters, with an overall exhaustion value occurring for the part thus far able to be determined in the result. On the basis of this accumulated exhaustion value the expected remaining lifetime of the part can then be predicted, with a maintenance or replacement interval for the part being able to be defined on the basis of the relevant characteristic exhaustion parameters determined to meet particular requirements.

In accordance with the invention the object is achieved by also taking into account for the determination of the characteristic value, in addition to any load cycles which have been fully completed, a load cycle which has only been partly completed, with a temporary stress values for phases of the partly completed load cycle not yet executed being taken into account with a predetermined fixed value.

In this case the invention uses as its starting point the idea that even a method suitable for a comparatively timely prediction of the current fatigue state of a part should be designed to be independent of possible comparatively long time intervals in the ending of a stress cycle. In order to still be able to output a comparatively reliable prognosis about the current fatigue state, the method should however not be restricted to evaluating the load cycles already completed in the past. This can be achieved by also taking into account knowledge about the current load cycle which already exists but has not yet been completed in determining the approximate value of the parameter characteristic of the fatigue state, even if a comparatively high inaccuracy may possibly have to be taken into account for this parameter because of the only incomplete data available of the current stress cycle. In order to achieve this, measured values actually already present should also be taken into account to the greatest possible extent in the stress cycle currently being run but not yet completed, in which case, to allow further processing of the not yet available characteristic stress values for the phases not yet run of the partly completed load cycle, a suitable fixed value as a type of placeholder is predetermined as a substitute value.

The fixed value predetermined as the temporary stress value for the phases of the partly completed load cycle not yet executed can in this case be selected with particular reference to available, possibly material-specific or part-specific knowledge. To make further evaluation especially simple however a zero value is advantageously predetermined as the fixed value.

The approximate determination of the parameter characteristic for the current fatigue state of the part is preferably undertaken on the basis of determining an intermediate value based on the load values determined for the current load cycle executed, with the intermediate value being able to be suitably transformed on the basis of stored databases into the actual parameter characteristic for the fatigue state. In this case the difference between the global maximum and the global minimum of a load cycle is advantageously formed for determining the approximate parameter.

Depending on the development of external circumstances over time and possibly varying operational requirements, a load cycle can also feature local maxima or minima in addition to the global maxima and minima which occur as a rule. To also allow an especially accurate determination of the parameter characteristic for the fatigue state for the situation in which the global minimum of the not yet completed load cycle is not yet reached and thus the corresponding knowledge is not yet available, an intermediate value for determining the approximate value is advantageously formed from the global maximum and a local minimum of a load cycle.

The method can be used especially advantageously for components or parts which are subjected as a condition of their operation to a comparatively extended load cycle in terms of time, since precisely with these types of parts or components the complete ending of the current load cycle or stress cycle otherwise required for the evaluation can lead to a comparatively large time deviation from the current actual state in the determination of the fatigue state. The method is thus advantageously used in heavy mechanical engineering, especially in a power plant, preferably in the operation of a steam turbine system.

The advantages achieved with the invention lie especially in the fact that, by taking into account the phases of the partly completed load cycle which have not yet been run with a predetermined fixed value for the relevant stress value, an especially timely determination of the exhaustion state of the relevant part is made possible without having to initially wait for the total completion of the current load cycle. In this case at least the knowledge already available of the current load cycle can also be taken into account so that for the relevant part, even within an incomplete load cycle, at least one approximate parameter characteristic for the at least already reached exhaustion or material fatigue can be determined. In this case, even with load cycles which extend over a comparatively long period, comparatively high quality prognoses about the current material state and about possible residual lifetimes, required maintenance work and such like are made possible. In addition, in the event of the failure of a part for example, a better diagnosis is made possible since an exhaustion occurring can be determined close in time to the underlying causes so that it is possible to assign the exhaustion which has occurred comparatively precisely to the possible cause.

BRIEF DESCRIPTION OF THE DRAWING

An exemplary embodiment of the invention is explained in more detail below with reference to a sole drawing. The sole FIGURE shows, in the form of a diagram, the possible timing curve of a stress cycle of a component during operation of a steam turbine.

DETAILED DESCRIPTION OF INVENTION

In the normal operating mode of a steam turbine, in a start or start-up phase, starting from the stationary turbine, there is a successively increasing application of a working medium at high temperature, which leads to the heating up especially of the components in contact with the medium. The heating up of the components directly exposed to the medium, such as the turbine blades for example or other parts directly exposed to medium, occurs in this case initially by a comparatively rapid warming up of the surfaces directly exposed to the medium, which as a result of the thermal inertia, depending on material and construction of the relevant component, especially of the relevant wall strength, propagates more quickly or less quickly into the internal area of the component concerned. In a transitional phase while the steam turbine is starting up, this means that, in a few components, there is a temperature difference between the outer side or surface on the one hand and the internal area on the other hand of the respective component. This temperature difference results in a thermal stress in the respective component which is basically comparable to a mechanical stress, for example a compression stress.

When the steam turbine cools down on the other hand the cooling-down of the respective component occurs by the surface cooling off first and this increasing cooling-off propagating into the interior of the respective component. During this operating phase of the steam turbine a temperature difference likewise arises between the component surface and the component interior on individual components of the steam turbine, with the surface being colder than the interior of the respective component in this phase however. The thermal stresses resulting from this typically correspond to a mechanical tensile stress of the components.

The tension-induced stresses on the respective parts of the steam turbine occurring during this type of operating mode can for example be represented as what is known as a load-time a diagram, such as is shown in the case of a steam turbine for example as diagram 1 in the FIGURE. The time t is plotted in this case on the x axis of diagram 1, with in the exemplary embodiment, a characteristic value determined for the temperature difference ΔT between the surface of a selected part of the steam turbine, for example the turbine housing, and the temperature in its interior, is plotted on the y axis. This temperature difference is characteristic for the thermal stresses occurring in the part and thereby also for the mechanical stresses induced by them. Alternatively, for example for other parts of the steam turbine or also for other parts of another technical system, another value characteristic of the stress on the part such as for example a mechanical stress or such like, could be plotted on the y axis of diagram 1.

The stress cycle shown in its entirety in diagram 1 of the part of the steam turbine begins at point in time $t_1$ with the start phase of the steam turbine. From point in time $t_1$ onwards, the steam turbine is increasingly heated up so that a positive temperature difference arises between the surface and the interior of the respective part. In this phase the characteristic stress curve 2 in diagram 1 for the stress cycle initially increases. On further heating up of the steam turbine this temperature difference initially increases further until it reaches a maximum 4 at point in time $t_2$.

As the state of equilibrium is increasingly approached the temperature difference subsequently starts to decrease again, until, at point in time $t_3$, a state of equilibrium is achieved in which an even temperature distribution is present within the respective part. In the exemplary embodiment shown in diagram 1 there is subsequently, depending on the type of operating mode, a slight cooling-off of the components, which this likewise taking place starting from the surface of the part and extending into its interior. Thus a negative temperature difference arises between the surface and the interior of the part. At point in time $t_4$ the amount of this temperature difference is at its maximum so that a minimum 6 is formed in the stress curve 2. Subsequently the temperatures of the surface and the interior of the part once again equalize so that the stress curve 2 again tends towards a zero value.

In the exemplary embodiment however, before this point is reached, there is a renewed cooling-off of the steam turbine so that the amount of the temperature difference between surface and interior of the part grows once more. This results, at point in time $t_5$, in a local maximum 8 of the load curve 2. Starting from this value, the amount of the temperature difference increases further and forms, at point in time $t_6$, a further minimum 10 in the load curve 2. Starting from this point, the temperatures again approach one another, whereby, depending on operational factors, after passing through a further maximum 12 and a further minimum 14, at point in time $t_7$ the steam turbine is completely cooled off and the temperature difference between surface and interior of the selected component again assumes the value zero.

In the period between the points in time $t_1$ and $t_7$, the steam turbine thus passes through a complete stress cycle with heating up and cooling down of the selected part. As a result of the microscopic rearrangement processes produced by the stresses shown, when a part passes through this type of stress cycle—also called a load cycle—a weakening of the part—also referred to as fatigue or exhaustion of the material—occurs, resulting in reduced mechanical ability to withstand loads and such like. The lifetime of the respective part is in this case restricted especially by the weakening or fatigue associated with said stressing, so that, if a material exhaustion or fatigue viewed as permissible for the part is exceeded overall, an exchange or a repair of the respective part is seen as necessary.

A characteristic parameter for the exhaustion state of the part can in such cases be assigned on the basis of part and material-specific empirical values, which can be stored in a database for example. For assignment of a approximate parameter characteristic for this exhaustion, the stress cycle illustrated in diagram 1 is evaluated by the so-called load cycle given by the difference between the global maximum 4 and the global minimal 10, symbolized by the arrow 16 being computed. An estimated value for the additional fatigue can be assigned to this based on previous experience, if necessary using data stored in a database, which the part has experienced after passing through the entire stress cycle represented by the stress curve 2. This additional fatigue can be added into a type of cumulative evaluation to previous exhaustion and characteristic values determined on the basis of previous stress cycles for the part, so that a parameter is produced which is characteristic for the overall exhaustion present for the respective part. A statement can then be obtained from this for example about the residual lifetime of the part, a prognosis for future maintenance intervals or a diagnostic statement or such like.

Precisely in the example of the stressing of a component of a steam turbine shown, the overall stress cycle executed can however extend over a significant period of time, for example over months or years. In order in this case not to have to depend for the determination of the approximate parameter characteristic the current fatigue state of the part on the complete sequence of the current stress cycle and to be able to make a high quality prognosis statement in an especially timely manner, in the determination of the approximate parameter characteristic for the fatigue state of the part as a result of the time-varying characteristic value for the load, in addition to the if necessary already completed load cycles, there is provision to also take account of a partly completed load cycle, in which case temporary stress values for phases of the partly completed load cycle not yet executed are taken into account, with a zero value as predetermined fixed value.

Thus for example, at a point in time after the curve passes through a first maximum 4, i.e. at a point in time after point in time $t_2$, the approximate value of the parameter characterizing the fatigue state of the component is determined with the proviso that the as yet uncompleted load cycle is included by taking account of the previous maximum stress indicated by the double arrow 18. To this end the further possibly relevant characteristic values, i.e. typically the temporary stress in the global minimum 10 which the curve has not yet passed through, are used in the underlying calculation as zero values. By contrast, after the curve has passed through the local minimum 6, the previous maximum amount of stress indicated by the double arrow 20, given by evaluating the global maximum 4 and the local maximum 6, is taken into account as an intermediate value for determining the characteristic parameter.

The invention claimed is:
1. A method for determining an approximate value for a parameter characteristic of a fatigue state of a component as a result of a time-varying stress, comprising:
   determining the approximate value based upon a partly completed load cycle, including;
   determining a temporary stress value for a unexecuted phase of the partly completed load cycle by a predetermined values and determining an intermediate value, wherein the intermediate value is determined based upon a difference between a global maximum and a global minimum of a previously occurred phase of the partly completed load cycle, and operating the component with consideration of a statement of a residual lifetime or a prognosis of a future maintenance interval of the component based on the approximate value.

2. The method as claimed in claim 1, wherein the predetermined value is fixed.

3. The method as claimed in claim 1, wherein the predetermined value is zero.

4. The method as claimed in claim 1, wherein an overall stress cycle extends over months.

5. The method as claimed in claim 1, wherein an overall stress cycle extends over years.

6. The method as claimed in claim 1, wherein a tension-induced stress on the component is represented in a load-time diagram.

7. The method as claimed in claim 1, wherein the component is a component of a turbine.

8. The method as claimed in claim 7, wherein turbine is a steam turbine.

* * * * *